(12) United States Patent
Bibal et al.

(10) Patent No.: US 8,470,940 B2
(45) Date of Patent: Jun. 25, 2013

(54) COMPLEXES AND METHOD FOR SYNTHESIS OF GROUP 4 ORGANOMETALLICS GRAFTED ON ANIONS OLEFIN OLIGOMERIZATION AND POLYMERIZATION METHOD

(75) Inventors: Christine Bibal, Castres (FR); Catherine Santini, Collonges au Mont d'Or (FR); Yves Chauvin, Tours (FR); Helene Olivier-Bourbigou, Saint Genis-Laval (FR); Christophe Vallee, Sassenage (FR)

(73) Assignee: IFP Energies nouvelles, Rueil-Malmaison Cedex (FR)

( * ) Notice: Subject to any disclaimer, the term of this patent is extended or adjusted under 35 U.S.C. 154(b) by 495 days.

(21) Appl. No.: 12/667,557

(22) PCT Filed: Jul. 3, 2008

(86) PCT No.: PCT/FR2008/000954
§ 371 (c)(1),
(2), (4) Date: Jul. 21, 2010

(87) PCT Pub. No.: WO2009/024675
PCT Pub. Date: Feb. 26, 2009

(65) Prior Publication Data
US 2010/0286349 A1    Nov. 11, 2010

(30) Foreign Application Priority Data
Jul. 5, 2007    (FR) .................................... 07 04935

(51) Int. Cl.
| | | |
|---|---|---|
| C08F 4/52 | (2006.01) | |
| C08F 4/64 | (2006.01) | |
| C08F 4/76 | (2006.01) | |
| B01J 31/38 | (2006.01) | |
| C07F 7/00 | (2006.01) | |

(52) U.S. Cl.
USPC ........... 526/113; 526/114; 526/172; 526/161; 526/348; 502/103; 502/104; 556/51; 556/7

(58) Field of Classification Search
USPC .. 556/51, 7; 526/134, 160, 170, 113; 502/103
See application file for complete search history.

(56) References Cited

U.S. PATENT DOCUMENTS
2005/0215738 A1    9/2005    Goodall et al.

FOREIGN PATENT DOCUMENTS
| | | |
|---|---|---|
| FR | 2829133 A1 | 3/2003 |
| WO | 2005090373 A1 | 9/2005 |

OTHER PUBLICATIONS

Bibal et al., Dalton Trans., 2008, 2866-2870.*
Carr, A. G.; Dawson, D.M.; Bochmann, M. Macromolecules, 1998, 31, 2035-2040.*
Rodriguez-Delgado, A.; Chen, E.Y.-X. Inorg. Chim. Acta, 2004, 357, 3911-3919.*
Seidle, A.R.; Newmark, R.A.; Lamanna, W.M. Organometallics, 1993, 12, 1491-1492.*
Rodriguez-Delgado A et al: "Ligand exchange and abstraction reactions involving titanium isopropoxide with tris (pentafluorophenyl) borane and -alane: ramifications for ring-opening polymerization of propylene oxide" (Inorganica Chima Acta) Nov. 1, 2004, pp. 3911-3919, vol. 357 No. 13.
Mandal Swadhin K et al: "Synthesis, Structural Characterization, and Theoretical Investigation of Compounds Containing an Al-O-M-O-Al (M=Ti, Zr) Core" (Inorganic Chemistry, American Chemical Society.) Jan. 1, 2007, pp. 7594-7600, vol. 46 No. 18.
Gurubasavaraj Prabhuodeyara M et al: "Synthesis, Structural Characterization, Catalytic Properties, and Theoretical Study of Compounds Containing an Al-O-M (M=Ti, Hf) Core" (Inorganic Chemistry, American Chemical Society.)Jan. 1, 2007, pp. 1056-1061, vol. 46 No. 4.
Choukroun R et al. "Disproportionation of Cationic Zirconium Complexes: A Possible Pathway to the Deactivation of Catalytic Cationic Systems." (Organometallics, ACS) Jan. 1, 1997, pp. 5517-5521, vol. 16 No. 1.
World IP Organization. "International Search Report." PCT/FR2008/000954, Applicant: IFP, Mailed Mar. 3, 2009.
Espacenet Database. "English Abstract-Catalytic composition, for alkylation of aromatic hydrocarbons, comprises Bronsted acid(s) dissolved in non-aqueous liquid medium with ionic nature." FR2829133A1, Applicant: IFP, Mar. 7, 2003.
Wang X et al. "Polyoxometalates supporting cyclopendienylzirconium CpZrXW11039n-: a new kind of olefin polymerization catalyst" (Inorganic Chemistry Communications) Jan. 1, 2005, pp. 70-71, vol. 8 No. 1.
World IP Organization. "International Search Report." PCT/FR2008/000954, Applicant: IFP, Mailed: Mar. 3, 2009.

* cited by examiner

*Primary Examiner* — Rip A. Lee
(74) *Attorney, Agent, or Firm* — Millen, White, Zelano & Branigan, P.C.

(57) ABSTRACT

Novel group 4 organometallic compounds, supported on anions by means of at least one covalent metal-oxygen bond, are obtained by reaction of at least one borate or aluminum comprising at least one hydroxy group with at least one group 4 transition metal compound. These compounds are used in a catalytic composition implemented in an olefin oligomerization or polymerization method.

28 Claims, No Drawings

COMPLEXES AND METHOD FOR SYNTHESIS OF GROUP 4 ORGANOMETALLICS GRAFTED ON ANIONS OLEFIN OLIGOMERIZATION AND POLYMERIZATION METHOD

FIELD OF THE INVENTION

The present invention relates to novel group 4 organometallic complexes supported on anions by means of at least one covalent metal-oxygen bond. It also relates to a method for synthesis of these compounds. It furthermore describes an olefin oligomerization or polymerization method implementing a catalytic composition resulting from the present invention.

BACKGROUND OF THE INVENTION

Homogeneous organometallic catalysts are used industrially for olefin oligomerization and polymerization. For example, the Dimersol® process for dimerization of light olefins or the Alphabutol® process for selective dimerization of ethylene use homogeneous catalysts based on nickel or titanium respectively.

These organometallic catalysts generally have a high activity and excellent selectivity resulting from the unicity of the active site and the coordination sphere control of the metal.

Despite such advantages, these catalysts are likely to deactivate by interaction of the organometallic species in solution, via polynuclear species formation or dismutation mechanisms (*Organometallics*, 1997, 5517-5521). These interactions are favoured by the absence of repulsion between the metal centres. Besides, recycling homogeneous catalysts and/or separating them from reaction products are delicate operations in homogeneous processes.

Surface organometallic chemistry was developed to overcome these drawbacks (*Angew. Chem. Inter. Ed.* 2003, 42, 156-181). Homogeneous catalysts grafted on an oxide surface are recyclable and the metal centres anchored to the surface are not likely to interact with one another. However, this methodology suffers from the heterogeneity of the surface sites of a solid, which leads to a multiplicity of active sites (*J. Am. Chem. Soc.* 2006, 128, 9361-9370). It is furthermore difficult to control the metal content of the solid obtained or to modify the environment of the metal in order to vary the catalysis properties thereof.

A Göttingen University team has described the polymerization of ethylene catalyzed by p-oxo-heterobimetallic complexes having Al—O-M bonds, where M is a group 4 metal (*Inorg. Chem.* 2007, 46, 1056-1061; *Inorg. Chem.* 2007, 46, 7594; WO-2005/090,373). However, these complexes are neutral entities and the interactions between the catalytic centres in solution are therefore not limited by charge repulsion.

We have discovered that grafting organometallic compounds on an anion by means of at least one covalent metal-oxygen bond allows to overcome these limitations. The species formed thus has an anionic character, which affords several advantages:
- the interactions between the metal centres in solution are therefore limited, as a result of the charge repulsion, and
- the entity formed is soluble in ionic solvents, which opens up the possibility of immobilizing and recycling it to a two-phase technology.

DETAILED DESCRIPTION

The present invention describes group 4 organometallic compounds supported on anions by means of at least one covalent metal-oxygen bond, of general formula I or II.

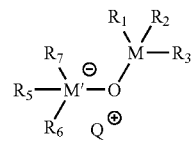

I

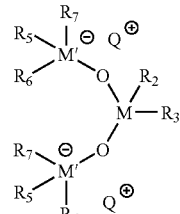

II

These products are obtained by reaction of at least one borate or aluminate type compound (A) comprising at least one hydroxy group with at least one group 4 transition metal compound (B).

The present invention also describes a mixture of group 4 organometallic compounds supported on anions by means of at least one covalent metal-oxygen bond, obtained by reaction between at least one compound A and at least one compound B.

The present invention describes a method for synthesis of group 4 organometallic compounds supported on anions by means of at least one covalent metal-oxygen bond, obtained by reacting at least one compound A with at least one compound B.

The present invention also describes a catalytic composition comprising:
- at least one borate or aluminate type compound A comprising at least one hydroxy group,
- with at least one group 4 transition metal compound B,
- at least one activator agent, and
- optionally a solvent.

The present invention also describes a catalytic composition resulting from contacting:
- at least one group 4 organometallic compound of general formula I or II, supported on anions by means of at least one covalent metal-oxygen bond,
- with at least one activator agent, and
- optionally a solvent.

The present invention furthermore describes an olefin oligomerization or polymerization method implementing said catalytic compositions.

The presence of the covalent metal-oxygen bond is evidenced in the present invention by means of the spectroscopic analysis techniques commonly known to and used by the person skilled in the art (proton, carbon, fluorine and boron NMR, mass spectrometry and IR spectrometry).

Compound A

According to the present invention, the borate or aluminate type compound A comprising at least one hydroxy group can be described by the general formula as follows:

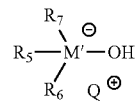

A wherein M' represents boron or aluminium, $q^+$ represents an organic or inorganic cation. $R_5$, $R_6$ and $R_7$, identical or different, represent organic radicals having 1 to 30 carbon atoms, for example alkyl groups, saturated or non-saturated, cycloalkyl or aromatic groups, aryl or aralkyl groups, possibly substituted.

$R_5$, $R_6$ and $R_7$, identical or different, can also represent hydrocarbyl radicals wherein one or more hydrogen atoms are replaced by halogenides or groups comprising at least one heteroelement such as an oxygen, a nitrogen, a sulfur or a silicon.

$R_5$, $R_6$ and $R_7$, identical or different, can also represent alkoxy, aryloxy or amidide groups.

Preferably, $R_5$, $R_6$ and $R_7$ represent the pentafluorophenyl or 3,5-(bistrifluoromethyl)phenyl radicals.

Preferably, cation $Q^+$ is an organic cation. It is preferably selected from the group made up of phosphonium, ammonium, guanidinium and/or sulfonium.

In the formulas hereafter, $X^1$, $X^2$, $X^3$, $X^4$, $X^5$ and $X^6$ represent hydrogen, preferably a single substituent representing hydrogen, or hydrocarbyl radicals having 1 to 30 carbon atoms, for example alkyl groups, saturated or non-saturated, cycloalkyl or aromatic groups, aryl or aralkyl groups, possibly substituted.

More preferably, $X^1$, $X^2$, $X^3$, $X^4$, $X^5$ and $X^6$ represent hydrocarbyl radicals having 1 to 30 carbon atoms, for example alkyl groups, saturated or non-saturated, cycloalkyl or aromatic groups, aryl or aralkyl groups, possibly substituted.

The sulfonium and guanidinium cations preferably meet one of the general formulas $SX^1X^2X^{3+}$ or $C(NX^1X^2)(NX^3X^4)(NX^5X^6)^+$, where $X^1$, $X^2$, $X^3$, $X^4$, $X^5$ and $X^6$, identical or different, are defined as above.

The quaternary ammonium and/or phosphonium cations $Q^+$ preferably meet one of the general formulas $NX^1X^2X^3X^{4+}$ and $PX^1X^2X^3X^{4+}$, or one of the general formulas $X^1X^2N=CX^3X^{4+}$ and $X^1X^2P=CX^3X^{4+}$, where $X^1$, $X^2$, $X^3$ and $X^4$, identical or different, are defined as above.

The ammonium and/or phosphonium cations can also be derived from nitrogen-containing and/or phosphorus-containing heterocycles comprising 1, 2 or 3 atoms of nitrogen and/or phosphorus, of general formulas:

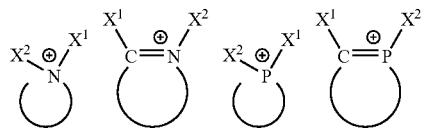

wherein the cycles consist of 4 to 10 atoms, preferably 5 to 6 atoms, and $X^1$ and $X^2$, identical or different, are defined as above.

The quaternary ammonium or phosphonium cation can also meet one of the following general formulas: $X^1X^{2+}N=CX^3-X^7-X^3C=N^+X^1X^2$ and $X^1X^2P=CX^3-X^7-X^3C=P^+X^1X^2$, wherein $X^1$, $X^2$ and $X^3$, identical or different, are defined as above, and $X^7$ represents an alkylene or phenylene radical.

Among the $X^1$, $X^2$, $X^3$ and $X^4$ groups, the following radicals can be mentioned: methyl, ethyl, propyl, isopropyl, primary butyl, secondary butyl, tertiary butyl, butyl, amyl, phenyl or benzyl; $X^7$ can be a methylene, ethylene, propylene or phenylene group.

Examples of borate or aluminate type compounds that can be used in the present invention are: butyl-3-methyl-1-imidazolium tris-pentafluorophenyl-hydroxyborate, 1-butyl-2,3-dimethymimidazolium tris-pentafluorophenyl-hydroxyborate, 1-ethyl-3-methylimidazolium tris-pentafluorophenyl-hydroxyborate, 1-butyl-3-butylimidazolium tris-pentafluorophenyl-hydroxyborate, N,N-butylmethylpyrrolidinium tris-pentafluorophenyl-hydroxyborate, tetrabutylphosphonium tris-pentafluorophenyl-hydroxyborate, tetraphenylphosphonium tris-pentafluorophenyl-hydroxyborate, butyl-3-methyl-1-imididazolium tris-pentafluorophenyl-hydroxyaluminate, butyl-3-methyl-1-imidid-azolium tris-phenyl-hydroxyborate, butyl-3-methyl-1-imididazolium tris-[3,5-bis(tri-fluoromethyl)phenyl]-hydroxyborate.

Cation $Q^+$ can be an inorganic cation preferably selected from among groups 1 or 2 of the periodic classification (Li, Na, K, Mg or Ca).

Transition Metal Compound B

According to the present invention, group 4 transition metal compound B can be described by the general formula:

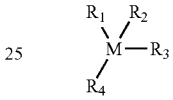

B

In this formula, M represents titanium, zirconium or hafnium. $R_1$, $R_2$, $R_3$ and $R_4$, identical or different, represent halogenides (F, Cl, Br, I) or organic radicals having 1 to 30 carbon atoms, preferably alkyl, cycloalkyl or aryl groups, possibly substituted, cyclopentadienyls, substituted or not (denoted by Cp), alkoxy, aryloxy, amidide, hydrido, carboxylate, oxalate, β-diketiminate, iminopyrrolide, amidinate or boratabenzene groups.

Preferably, among $R_1$, $R_2$, $R_3$ and $R_4$, there are at least two hydrocarbyl radicals, identical or different, preferably selected from among alkyls, cycloalkyls, aryls or aralkyls.

Group 4 transition metal compound B can be of monomeric, dimeric or oligomeric nature of higher order.

The adducts of the compounds of type B described above with a Lewis base can also be used according to the present invention. Examples of Lewis bases that can be used according to the present invention are ethers, amines, thioethers and phosphines.

Examples of B type compounds of a group 4 transition metal that can be used according to the present invention are: $ZrCl_4$, $Zr(CH_2Ph)_4$, $Zr(CH_2CMe_3)_4$, $Zr(CH_2SiMe_3)_4$, $Zr(CH_2Ph)_3Cl$, $Zr(CH_2CMe_3)_3Cl$, $Zr(CH_2SiMe_3)_3Cl$, $Zr(CH_2Ph)_2Cl_2$, $Zr(CH_2CMe_3)_2Cl_2$, $Zr(CH_2SiMe_3)_2Cl_2$, $Zr(NMe_2)_4$, $Zr(NEt_2)_4$, $Zr(NMe_2)_2Cl_2$, $Zr(NEt_2)_2Cl_2$ and $Zr(N(SiMe_3)_2)_2Cl_2$, $Cp_2ZrMe_2$, $CpZrMe_3$, $Cp^*ZrMe_3$ ($Cp^*$=penta-methylcyclopentadienyl), $HfCl_4$, $Cp_2HfMe_2$, $CpHfMe_3$, $Hf(CH_2Ph)_4$, $Hf(CH_2CMe_3)_4$, $Hf(CH_2SiMe_3)_4$, $Hf(CH_2Ph)_3Cl$, $Hf(CH_2CMe_3)_3Cl$, $Hf(CH_2SiMe_3)_3Cl$, $Hf(CH_2Ph)_2Cl_2$, $Hf(CH_2CMe_3)_2Cl_2$, $Hf(CH_2SiMe_3)_2Cl_2$, $Hf(NMe_2)_4$, $Hf(NEt_2)_4$ and $Hf(N(SiMe_3)_2)_2Cl_2$.

The adducts of these compounds with Lewis bases such as ethers, amines, thioethers or phosphines can also be used according to the present invention.

Organometallic Compounds I and II

According to the present invention, the organometallic compounds supported on anions by means of a covalent metal-oxygen bond can be described by general formulas I or II wherein M, M', $R_1$, $R_2$, $R_3$, $R_5$, $R_6$, $R_7$ and $Q^+$ are defined as above.

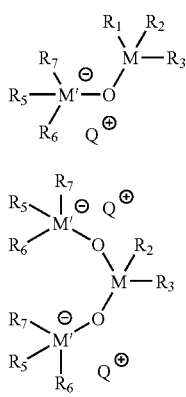

The adducts of anion-supported organometallic compounds with a Lewis base can also be used according to the present invention.

For the anion-supported organometallic compounds of general formula I, preferably at least two of the three groups $R_1$, $R_2$, $R_3$ are hydrocarbyl radicals selected from among the alkyl, cycloalkyl, aryl or aralkyl groups.

For the anion-supported organometallic compounds of general formula II, the two groups $R_2$ and $R_3$ are preferably hydrocarbyl groups selected from among the alkyl, cycloalkyl, aryl or aralkyl groups.

Method for Synthesis of Monometallic Complexes I and II

The synthesis of group 4 organometallic compounds supported on anions by means of at least one covalent metal-oxygen bond of general formula I or II is achieved through the reaction of a borate or aluminate compound A comprising at least one hydroxy group with a group 4 transition metal compound B.

The reaction can be carried out simply by contacting, followed by stirring of compound A with compound B, optionally in the presence of a solvent. Addition of the various constituents can be performed in any order.

The reaction can preferably be carried out by adding compound A to compound B in a solvent.

The solvent can be selected from the group of organic solvents. The organic solvents preferably are aprotic solvents. Examples of solvents that can be used in the synthesis method according to the present invention are hydrocarbons such as pentane, hexane, cyclohexane or heptane, aromatic hydrocarbons such as benzene, toluene or xylenes, chlorinated solvents such as dichloromethane, or acetone, acetonitrile, diethylether, THF, DMSO and DMF.

The solvent used for the synthesis of I and II can also be an ionic liquid. The ionic liquid preferably consists of a cation $Q^+$ as defined above, associated with an organic or inorganic anion. The cation $Q^+$ preferably is an organic cation. The anion is preferably selected from among halegonide anions, nitrate, sulfate, alkylsulfates, phosphate, alkylphosphates, acetate, halogenoacetates, tetrafluoroborate, tetrachloroborate, hexafluorophosphate, trifluoro-tris-(pentafluoroethyl) phosphate, hexafluoroantimonate, fluorosulfonate, alkylsulfonates (for example methylsulfonate), perfluoroalkylsulfonates (for example trifluoromethylsulfonate), bis(perfluoroalkylsulfonyl)amidides (for example bis trifluoromethylsulfonyl amidide of formula $N(CF_3SO_2)_2^-$), tris-trifluoromethylsulfonyl methylide of formula $C(CF_3SO_2)_3^-$, bis-trifluoromethylsulfonyl methylide of formula $HC(CF_3SO_2)_2^-$, arenesulfonates, possibly substituted by halogen or halogenoalkyl groups, the tetraphenylborate anion and the tetraphenylborate anions whose aromatic rings are substituted, tetra-(trifluoroacetoxy)-borate, bis-(oxalato)-borate, dicyanamide and tricyanomethylide.

A mixture of organic solvents and/or of ionic liquids can be used for the synthesis method according to the present invention.

The molar ratio of A to B can range between 0.1/1 and 100/1. Preferably, the molar ratio ranges between 1/1 and 10/1, more preferably between 1/1 and 2/1.

The temperature of the reaction between A and B ranges between −100° C. and 150° C., preferably between −78° C. and 50° C.

Compounds I or II can be isolated by means of conventional methods used in coordination chemistry or organic synthesis, for example by precipitation or crystallization in an organic solvent or a mixture of organic solvents.

The reaction between A and B leads to the formation of various compounds to which compounds I and II belong. By way of example, it is also possible to obtain compounds III or IV:

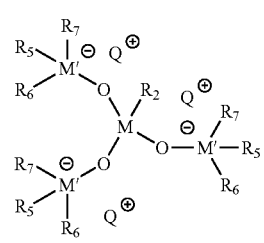

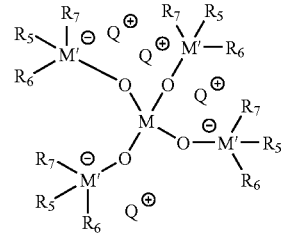

Olefin Oligomerization or Polymerization Method

The organometallic compounds described above are now going to be described more precisely within the context of their use as a catalytic composition for an olefin oligomerization or polymerization method.

This catalytic composition comprises the following characteristic elements:
  i) at least one type I or II compound,
  ii) at least one activator agent, and
  iii) optionally a solvent.

The catalytic system can also be generated "in situ" in the reactor. The catalytic composition results then from contacting the following characteristic elements:
  i) at least one compound A,
  ii) at least one compound B,
  iii) at least one activator agent, and
  iv) optionally a solvent.

Activator Agent

The activator agent is a compound that generates an active catalytic species. This activator agent can be contacted with the precursors of the catalytic system, either "in situ" in the catalytic reactor or "ex situ" prior to injecting the catalytic composition into the reactor, the precursors of the catalytic system being compounds I or II, or the products resulting from the reaction between at least one compound A and one compound B.

The activator agent can be a Lewis acid, a Bronsted acid, an alkylating agent or any compound likely to hydrogenolyze a metal-carbon bond.

The activator agent is preferably selected from among the alkylating agents when compounds I and II or compound B, from which they originate, comprise no group 4 metal-carbon bond, i.e. when none of groups $R_1$, $R_2$, $R_3$ and $R_4$ is a hydrocarbyl radical.

Preferably, the activator agent is selected from among aluminium derivatives such as, for example, aluminoxanes, organo-aluminiums, aluminium halogenides, aluminates; boron derivatives such as, for example, boranes or borates, zinc derivatives such as, for example, organo-zincs; Bronsted acids of $H^+X^-$ type; hydrogen.

By way of example, the organo-aluminiums that can be used as activators in the catalytic composition according to the invention are of general formula $AIR_nX'_{(3-n)}$, with n ranging between 1 and 3, the groups R, identical or different, being selected from among the alkyl, aryl or aralkyl groups having 1 to 12 carbon atoms and the X', identical or different, being selected from among halogenides, alkoxy, amidides, carboxylates. The organo-aluminiums are preferably selected from the trialkyl-aluminium group or from the dialkylaluminium chloride group or from the alkylaluminium dichloride group.

The aluminium halogenides that can be used as activators in the catalytic composition according to the invention are of general formula $AIX_3$, wherein X preferably represents chlorine or bromine.

The aluminoxanes that can be used as activators in the catalytic composition are selected from among alkylaluminoxanes such as methylaluminoxane (MAO) or ethylaluminoxane (EAO), or among modified alkylaluminoxanes such as modified methylaluminoxane (MMAO).

The boranes that can be used as activators in the catalytic composition are preferably selected from the tris-aryl-borane group wherein one or more hydrogen atoms of the aromatic ring can be replaced by halogenides or groups comprising at least one heteroelement such as an oxygen, a nitrogen, a sulfur or a silicon.

The boranes are preferably selected from the tris-perfluoroaryl-borane group.

Boranes having two or more Lewis acid sites, as described in document WO-99/06,413 or in *J. Am. Chem. Soc.* 1999, 121, p. 3244-3245, can also be used according to the present invention.

Examples of boranes that can be used according to the present invention are tris-pentafluorophenyl-borane, tris-phenyl-borane, tris-[3,5-bis(trifluoromethyl)-phenyl]-borane, tris(2,2',2"-perfluorobiphenyl)borane.

The borates are preferably selected from among the tetrakis-aryl-borates, such as tetraphenylborate, or the tetrakis-perfluoro-aryl-borates, such as tetrakis-penta-fluoroaryl-borate or the tetrakis-[3,5-bis(trifluoromethyl)phenyl]-borate salt. The borate salt cations are selected from among the ammonium cations such as triethylammonium, phosphonium such as triphenylphosphonium or triphenylcarbenium. The tetrakis-[3,5-bis(trifluoromethyl)phenyl]-borate salt $(Et_2O)_2 H^+$ can also be used for the present invention.

Examples of borate salts that can also be used as the activator agent for the present invention are also triphenylcarbenium borate, such as tetrakis-pentafluorophenyl-borate-triphenylcarbenium $[(Ph)_3C]^+[B(C_6F_5)_4]$, as described in patent EP-A-0,427,696. Other associated borate salts that can be used as the activator agent for the present invention are described in patent EP-A-0,277,004.

The organozincs are preferably selected from among the di-alkyl-zinc compounds.

The Bronsted type acids used according to the invention as activator agents are defined as organic compounds likely to give at least one proton. The formula of these acids is $H^+X^-$, wherein $X^-$ represents an anion.

The anions $X^-$ are preferably selected from among the following anions: tetrafluoroborate, tetraalkylborates, hexafluorophosphates, hexafluoroantimonates, alkylsulfonates (for example methylsulfonate), perfluorosulfonates (for example trifluoromethylsulfonate), fluorosulfonates, sulfates, phosphates, perfluoroacetates (for example trifluoroacetate), perfluorosulfonamides (for example bis-trifluoromethanesulfonyl amidide of formula $N(CF_3SO_2)_2$), fluorosulfonamides, perfluoro-sulfomethides (for example tris-trifluoromethanesulfonyl methylide of formula $C(CF_3SO_2)_3$), carboranes, tetraphenylborates and the tetraphenylborate anions whose aromatic rings are substituted.

The acids $H^+X^-$ used according to the invention can be used alone or in admixture.

It is possible to use, for the present invention, a mixture of several activator agents as defined above.

The Olefin Oligomerization or Polymerization Method

The olefin oligomerization or polymerization method according to the present invention optionally uses a solvent.

The solvent can be selected from the group of organic solvents and ionic liquids.

The organic solvent is preferably an aprotic solvent. Examples of solvents that can be used in the method according to the present invention are hydrocarbons, such as pentane, hexane, cyclohexane or heptane, aromatic hydrocarbons, such as benzene, toluene or xylenes, chlorinated solvents such as dichloromethane, or acetone, acetonitrile, diethylether, THF, DMSO and DMF. The organic solvent is preferably a hydrocarbon or aromatic hydrocarbon solvent.

The ionic liquid preferably consists of a cation $Q^+$ as defined above, associated with an organic or inorganic anion. Cation $Q^+$ preferably is an organic cation. The anion is preferably selected from among the following anions: halogenides, nitrates, sulfates, alkylsulfates, phosphates, alkylphosphates, acetates, halogenoacetates, tetrafluoro-borates, tetrachloroborates, hexafluorophosphates, trifluoro-tris-(pentafluoro-ethyl)phosphates, hexafluoroantimonates, fluorosulfonates, alkylsulfonates (for example methylsulfonate), perfluoroalkylsulfonates (for example trifluoromethylsulfonate), bis(perfluoroalkylsulfonyl)amidides (for example bis trifluoromethylsulfonyl amidide of formula $N(CF_3SO_2)_2^-$), tris-trifluoromethylsulfonyl methylide of formula $C(CF_3SO_2)_3^-$, bis-trifluoromethylsulfonyl methylide of formula $HC(CF_3SO_2)_2$, arenesulfonates, possibly substituted by halogen or halogenoalkyl groups, the tetraphenylborate anion and the tetraphenylborate anions whose aromatic rings are substituted, tetra-(trifluoroacetoxy)-borate, bis-(oxalato)-borate, dicyanamide and tricyanomethylide.

A mixture of organic solvents and/or of ionic liquids can be used for the oligomerization or polymerization method according to the present invention.

In the catalytic composition of the present invention, the molar ratio of [I or II] to activator agent ranges between 1/10,000 and 100/1, preferably between 1/500 and 1/1.

In the catalytic composition of the present invention, the molar ratio of [I or II] to activator agent preferably ranges between 1/50 and 1/1, more preferably between 1/2 and 1/1 when the activator agent is a Lewis acid, a Bronsted acid or any compound likely to hydrogenolyze a metal-carbon bond of [I or II], for the organometallic compounds of general formula I, of which at least two of the three groups $R_1$, $R_2$ and $R_3$ are hydrocarbyl radicals, and for the organometallic compounds of general formula II, of which the two groups $R_2$ and $R_3$ are hydrocarbyl radicals, the hydrocarbyl radicals being preferably alkyl, cycloalkyl, aryl or aralkyl groups.

In the catalytic composition of the present invention, the molar ratio of [I or II] to activator agent preferably ranges between 1/2000 and 1/1, more preferably between 1/500 and 1/1 when the activator agent is an alkylating agent.

In the catalytic composition of the present invention, the molar ratio of B to activator agent ranges between 1/10,000 and 100/1, preferably between 1/500 and 1/1.

In the catalytic composition of the present invention, the molar ratio of B to activator agent preferably ranges between 1/50 and 1/1, more preferably between 1/2 and 1/1 when the activator agent is a Lewis acid, a Bronsted acid or any compound likely to hydrogenolyze a metal-carbon bond of B, for the organometallic compounds of general formula B, of which at least three of the four groups $R_1$, $R_2$, $R_3$ and $R_4$ are hydrocarbyl radicals, preferably selected from among the alkyl, cycloalkyl, aryl or aralkyl groups.

In the catalytic composition of the present invention, the molar ratio of B to activator agent preferably ranges between 1/2000 and 1/1, more preferably between 1/500 and 1/1 when the activator agent is an alkylating agent.

In the catalytic composition of the present invention, the molar ratio of A to B ranges between 0.1/1 and 100/1. Preferably, the molar ratio of A to B ranges between 1/1 and 10/1, more preferably between 1/1 and 2/1.

The compounds that go into the catalytic composition according to the invention can be mixed in any order. Mixing can be achieved by simple contacting, followed by stirring until a homogeneous liquid forms. This mixing can be performed outside the oligomerization or polymerization reactor, or preferably in this reactor.

The method according to the present invention is particularly useful for olefin dimerization, co-dimerization, oligomerization or polymerization.

The olefins likely to be converted by the catalytic compositions according to the invention are more particularly ethylene, propylene, n-butenes and n-pentenes, alone or in admixture (co-dimerization), pure or diluted by an alkane, as can be found in "cuts" resulting from oil refining processes, such as catalytic cracking or steam cracking.

The catalytic olefin conversion reaction can be carried out in a closed system, a semi-open system or in a continuous system, with one or more reaction stages. Vigorous stirring provides proper contact between the reagent(s) and the catalytic composition.

The reaction temperature can range from −40° C. to +250° C., preferably from 0° C. to +150° C.

The heat generated by the reaction can be eliminated by any means known to the person skilled in the art. The pressure can range from atmospheric pressure to 20 MPa, preferably from atmospheric pressure to 10 MPa.

The following examples illustrate the invention without limiting the scope thereof.

ABBREVIATIONS USED IN THE EXAMPLES

BMI$^+$ or BMIM$^+$: 1-butyl-3-methylimidazolium
BMMI$^+$ or BMMIM$^+$: 1-butyl-2,3-dimethymimidazolium
EMI$^+$ or EMIM$^+$: 1-ethyl-3-methylimidazolium
BBI$^+$ or BBIM$^+$: 1-butyl-3-butylimidazolium
BMpy$^+$: N,N-butylmethylpyrrolidinium
Bu$_4$P$^+$: tetrabutylphosphonium
Ph$_4$P$^+$: tetraphenylphosphonium
Cp*: pentamethylcyclopentadienyl
Cp: cyclopentadienyl
NTf$_2^-$: bis trifluoromethylsulfonyl amidide of formula N(CF$_3$SO$_2$)$_2$

EXAMPLES

Examples of Compound A Preparation

Example 1

Preparation of [BMIM]$^+$[B(C$_6$F$_5$)$_3$OH]$^-$

A solution of 1-butyl-3-methyl imidazolium chloride (80 mg, 0.46 mmol, 1 eq) in dichloromethane (7 ml) is added dropwise to a solution of B(C$_6$F$_5$)$_3$ (234 mg, 0.46 mmol, 1 eq) in dichloromethane (7 ml), then the mixture is left under magnetic stirring for 12 h at ambient temperature. It is then added to a suspension of anhydrous lithium hydroxide (13 mg, 0.55 mmol, 1.2 eq) in dichloromethane (4 ml) at ambient temperature. After 12-h stirring, the LiCl precipitate is filtered and the solvent evaporated. The imidazolium tri-pentafluorophenyl-hydroxy-borate salt thus obtained is used in the subsequent synthesis stages. It is characterized by fluorine, proton, carbon and boron NMR, by mass spectrometry and IR spectroscopy. The NMR chemical shift of boron to −4.69 ppm, characteristic of the borate anion, can be noted in particular.

*NMR in C$_6$D$_6$
NMR $^{19}$F [282.4 MHz, C$_6$D$_6$] (δ, ppm): −135.9 (d, 6 F, $^3J_{FF}$=21.3 Hz, o-F); −161.7 (t, 3 F, $^3J_{FF}$=20.7 Hz, p-F); −165.8 (m, 6 F, m-F).
NMR $^1$H [300.1 MHz, C$_6$D$_6$] (δ, ppm): 0.64 (t, 3H, $^3J_{HH}$=7.4 Hz, CH$_3$); 0.75 (sext, 2H, $^3J_{HH}$=7.4 Hz, CH$_2$); 0.94 (quint, 2H, $^3J_{HH}$=7.4 Hz, CH$_2$); 2.09 (s, 1H, OH); 2.56 (s, 3H, CH$_3$); 3.04 (t, 2H, $^3J_{HH}$=7.4 Hz, CH$_2$); 5.32 (m, 1H, CH); 5.43 (m, 1H, CH); 9.19 (s, 1H, CH).
NMR $^{13}$C [75.5 MHz, C$_6$D$_6$] (δ, ppm): 13.07 (CH$_3$); 19.30 (CH$_2$); 31.63 (CH$_2$); 34.72 (CH$_3$); 49.08 (CH$_2$); 120.42 (CH(BMIM$^+$)); 121.84 (CH(BMIM$^+$)); 135.72 (CH(BMIM$^+$)); 137.57, 137.87, 139.11, 140.90, 147.25, 150.39 (CF).

*NMR in CD$_2$Cl$_2$
NMR $^{19}$F [282.4 MHz, CD$_2$Cl$_2$] (δ, ppm): −137.0 (d, 6 F, $^3J_{FF}$=21.3 Hz, o-F); −163.1 (t, 3 F, $^3J_{FF}$=20.7 Hz, p-F); −167.0 (m, 6 F, m-F).
NMR $^1$H [300.1 MHz, CD$_2$Cl$_2$] (δ, ppm): 0.92 (t, 3H, $^3J_{HH}$=7.4 Hz, CH$_3$); 1.29 (sext, 2H, $^3J_{HH}$=7.4 Hz, CH$_2$); 1.78 (quint, 2H, $^3J_{HH}$=7.4 Hz, CH$_2$); 1.84 (s, 1H, OH); 3.84 (s, 3H, CH$_3$); 4.07 (t, 2H, $^3J_{HH}$=7.4 Hz, CH$_2$); 7.21 (m, 2H, CH); 9.45 (s, 1H, CH).
NMR $^{13}$C [75.5 MHz, CD$_2$Cl$_2$] (δ, ppm): 13.32 (CH$_3$); 19.71 (CH$_2$); 32.29 (CH$_2$); 36.65 (CH$_3$); 50.47 (CH$_2$); 122.60 (CH(BMIM$^+$)); 123.89 (CH(BMIM$^+$)); 135.49 (CF); 136.97 (CH(BMIM$^+$)); 137.27, 138.69, 140.47, 146.73, 149.86 (CF).
NMR $^{11}$B [96.3 MHz, (CH$_2$Cl$_2$, 10% C$_6$D$_6$)] (δ, ppm): −4.69 (s).
ESI-MS: ESI(+) [M=139, BMIM$^+$], [M=806, [2×BMIM$^+$+B(C$_6$F$_5$)$_3$OH$^-$]+]; ESI(−) [M=529, B(C$_6$F$_5$)$_3$OH$^-$], [M=1196, [2×B(C$_6$F$_5$)$_3$OH$^-$+BMIM$^+$]$^-$].
IR [KBr]: ν(OH)=3679 cm$^{-1}$.

Example 2

Preparation of [Q]$^+$[B(C$_6$F$_6$)$_3$OH]$^-$: tri-pentafluorophenyl-hydroxyborate anions The tri-pentafluorophenyl-hydroxy-borate salts associated with the various imidazolium, pyrrolidinium or phosphonium cations $Q^+$ were prepared with quantitative yields according to the same method as that described in Example 1 for the 1-butyl-3-methyl imidazolium tri-pentafluorophenyl-hydroxy-borate salt.

These compounds are characterized by fluorine, proton, carbon and boron NMR, by mass spectrometry and IR spectrometry.

$Q^+$=imidazolium: Case of [BMMIM$^+$]; [EMIM$^+$]:

Characterization of [BMMIM$^+$][B(C$_6$F$_5$)$_3$OH$^-$]: Colourless Liquid.

NMR $^{19}$F [282.4 MHz, CD$_2$Cl$_2$] (δ, ppm): −136.8 (d, 6 F, $^3$J$_{FF}$=21.5 Hz, o-F); −163.7 (t, 3 F, $^3$J$_{FF}$=20.3 Hz, p-F); −167.4 (m, 6 F, m-F).

NMR $^1$H [300.1 MHz, CD$_2$Cl$_2$] (δ, ppm): 0.95 (t, 3H, $^3$J$_{HH}$=7.4 Hz, CH$_3$); 1.35 (sext, 2H, $^3$J$_{HH}$=7.4 Hz, CH$_2$); 1.67 (s, 1H, OH); 1.75 (quint, 2H, $^3$J$_{HH}$=7.4 Hz, CH$_2$); 2.58 (s, 3H, CH$_3$); 3.78 (s, 3H, CH$_3$); 4.03 (t, 2H, $^3$J$_{HH}$=7.4 Hz, CH$_2$); 7.21 (d, 1H, $^3$J$_{HH}$=2.1 Hz, CH); 7.27 (d, 1H, $^3$J$_{HH}$=2.1 Hz, CH).

NMR $^{13}$C [75.5 MHz, CD$_2$Cl$_2$] (δ, ppm): 9.86 (CH$_3$); 13.41 (CH$_3$); 19.88 (CH$_2$); 31.98 (CH$_2$); 35.76 (CH$_3$); 49.24 (CH$_2$); 121.53 (CH(BMMIM$^+$)); 123.14 (CH(BMMIM$^+$)); 135.32, 137.24, 138.63, 140.48 (CF); 143.80 (C(CH$_3$) (BMMIM$^+$)); 146.80, 149.96 (CF).

NMR $^{11}$B [96.3 MHz, (CH$_2$Cl$_2$, 10% CD$_2$Cl$_2$)] (δ, ppm): −4.52 (s).

ESI-MS: ESI(+) [M=153, BMMIM$^+$]; ESI(−) [M=529, B(C$_6$F$_5$)$_3$OH$^-$].

IR [KBr]: ν(OH)=3689 cm$^{-1}$.

Characterization [EMIM$^+$][B(C$_6$F$_5$)$_3$OH$^-$]: Colourless Liquid.

NMR $^{19}$F [282.4 MHz, CD$_2$Cl$_2$] (δ, ppm): −136.7 (d, 6 F, $^3$J$_{FF}$=22.1 Hz, o-F); −163.0 (t, 3 F, $^3$J$_{FF}$=20.1 Hz, p-F); −167.0 (m, 6 F, m-F).

NMR $^1$H [300.1 MHz, CD$_2$Cl$_2$] (δ, ppm): 1.48 (t, 3H, $^3$J$_{HH}$=7.4 Hz, CH$_3$); 1.90 (s, 1H, OH); 3.86 (s, 3H, CH$_3$); 4.16 (quart, 2H, $^3$J$_{HH}$=7.4 Hz, CH$_2$); 7.21 (m, 1H, CH); 7.25 (m, 1H, CH); 9.46 (s, 1H, CH).

NMR $^{13}$C [75.5 MHz, CD$_2$Cl$_2$] (δ, ppm): 15.32 (CH$_3$); 36.57 (CH$_3$); 45.82 (CH$_2$); 122.13 (CH(EMIM$^+$)); 123.91 (CH(EMIM$^+$)); 135.35 (CF); 137.0 (CH(EMIM$^+$)); 137.20, 138.63, 140.47, 146.72, 149.88 (CF).

NMR $^{11}$B [96.3 MHz, (CH$_2$Cl$_2$, 10% CD$_2$Cl$_2$)] (δ, ppm): −4.45 (s).

ESI-MS: ESI(+) [M=751, [2×EMIM$^+$+B(C$_6$F$_5$)$_3$OH$^-$]$^+$]; ESI(−) [M=529, B(C$_6$F$_5$)$_3$OH$^-$], [M=1169, [2×B(C$_6$F$_5$)$_3$OH$^-$+EMIM$^+$]$^-$].

IR [KBr]: ν(OH)=3685 cm$^{-1}$.

Characterization of [BBIM$^+$][B(C$_6$F$_5$)$_3$OH$^-$]: Colourless Liquid.

NMR $^{19}$F [282.4 MHz, CD$_2$Cl$_2$] (δ, ppm): −136.8 (d, 6 F, $^3$J$_{FF}$=21.8 Hz, o-F); −163.2 (t, 3 F, $^3$J$_{FF}$=20.3 Hz, p-F); −167.1 (m, 6 F, m-F).

NMR $^1$H [300.1 MHz, CD$_2$Cl$_2$] (δ, ppm): 0.93 (t, 6H, $^3$J$_{HH}$=7.5 Hz, CH$_3$); 1.29 (sext, 4H, $^3$J$_{HH}$=7.5 Hz, CH$_2$); 1.77 (quint, 4H, $^3$J$_{HH}$=7.5 Hz, CH$_2$); 1.81 (s, 1H, OH); 4.09 (t, 4H, $^3$J$_{HH}$=7.5 Hz, CH$_2$); 7.23 (bs, 1H, CH); 7.24 (bs, 1H, CH); 9.47 (s, 1H, CH).

NMR $^{13}$C [75.5 MHz, CD$_2$Cl$_2$] (δ, ppm): 13.35 (CH$_3$); 19.75 (CH$_2$); 32.34 (CH$_2$); 50.35 (CH$_2$); 122.52 (CH(BBIM$^+$)); 135.38 (CF); 136.63 (CH(BBIM$^+$)); 137.17, 138.64, 140.43, 146.72, 149.98 (CF).

NMR $^{11}$B [96.3 MHz, (CH$_2$Cl$_2$, 10% CD$_2$Cl$_2$)] (δ, ppm): −4.43 (s).

ESI-MS: [M=181, BBIM$^+$], [M=891, [2×BBIM$^+$+B(C$_6$F$_3$)$_3$OH$^-$]$^+$]; ESI(−) [M=529, B(C$_6$F$_5$)$_3$OH$^-$], [M=1239, [2×B(C$_6$F$_5$)$_3$OH$^-$+BBIM$^+$]$^-$].

IR [KBr]: ν(OH)=3683 cm$^{-1}$.

$Q^+$=pyrrolidinium: Case of [BMpy$^+$]

Characterization of [BMpy$^+$][B(C$_6$F$_5$)$_3$OH$^-$]: Colourless Liquid.

NMR $^{19}$F [282.4 MHz, CD$_2$Cl$_2$] (δ, ppm): −136.8 (d, 6 F, $^3$J$_{FF}$=21.9 Hz, o-F); −163.5 (t, 3 F, $^3$J$_{FF}$=20.0 Hz, p-F); −167.2 (m, 6 F, m-F).

NMR $^1$H [300.1 MHz, CD$_2$Cl$_2$] (δ, ppm): 0.98 (t, 3H, $^3$J$_{HH}$=7.7 Hz, CH$_3$); 1.38 (sext, 2H, $^3$J$_{HH}$=7.7 Hz, CH$_2$); 1.68 (s, 1H, OH); 1.70 (quint, 2H, $^3$J$_{HH}$=7.7 Hz, CH$_2$); 2.23 (bs, 4H, CH$_2$); 3.0 (s, 3H, CH$_3$); 3.25 (m, 2H, CH$_2$); 3.44 (m, 4H, CH$_2$).

NMR $^{13}$C [75.5 MHz, CD$_2$Cl$_2$] (δ, ppm): 13.53 (CH$_3$); 20.02 (CH$_2$); 22.05 (CH$_2$); 26.16 (CH$_2$); 49.19 (CH$_3$); 65.29 (CH$_2$); 65.38 (CH$_2$); 135.27, 137.22, 138.63, 140.40, 146.76, 149.94 (CF). RMN $^{11}$B [96.3 MHz, (CH$_2$Cl$_2$, 10% CD$_2$Cl$_2$)] (δ, ppm): −4.44 (s). SM-ESI:

ESI(+) [M=142, BMpy$^+$];
ESI(−) [M=529, B(C$_6$F$_3$)$_3$OH$^-$].

IR [KBr]: ν(OH)=3688 cm$^{-1}$.

$Q^+$=phosphonium: Case of [Bu$_4$P$^+$]; [Ph$_4$P$^+$]

Characterization of [Bu$_4$P$^+$][B(C$_6$F$_5$)$_3$OH$^-$]: Colourless Liquid.

NMR $^{19}$F [282.4 MHz, CD$_2$Cl$_2$] (δ, ppm): −136.8 (d, 6 F, $^3$J$_{FF}$=21.7 Hz, o-F); −163.8 (t, 3 F, $^3$J$_{FF}$=20.4 Hz, p-F); −167.3 (m, 6 F, m-F).

NMR $^1$H [300.1 MHz, CD$_2$Cl$_2$] (δ, ppm): 0.96 (t, 12H, $^3$J$_{HH}$=6.8 Hz, CH$_3$); 1.44-1.52 (m, 16H, CH$_2$); 1.64 (s, 1H, OH); 1.97-2.07 (m, 8H, PCH$_2$).

NMR $^{13}$C [75.5 MHz, CD$_2$Cl$_2$] (δ, ppm): 13.34 (CH$_3$); 19.01 (d, $^1$J$_{PC}$=48.0 Hz, PCH$_2$); 23.73 (d, $^2$J$_{PC}$=4.6 Hz, CH$_2$); 24.22 (d, $^3$J$_{PC}$=15.1 Hz, CH$_2$); 135.45, 137.03, 138.71, 140.30, 146.53, 146.90 (CF). RMN $^{11}$B [96.3 MHz, CD$_2$Cl$_2$] (δ, ppm): −4.50 (s).

NMR $^{31}$P [121.5 MHz, CD$_2$Cl$_2$] (δ, ppm): 33.41 (s) (1J$_{PC}$=47.7 Hz, $^2$J$_{PC}$=15.2 Hz).

ESI-MS: ESI(+) [M=259, Bu$_4$P$^+$]; ESI(−) [M=529, B(C$_6$F$_3$)$_3$OH$^-$].

IR [KBr]: ν(OH)=3689 cm$^{-1}$.

Characterization of [Ph$_4$P$^+$][B(C$_6$F$_5$)$_3$OH$^-$]: White Foam.

NMR $^{19}$F [282.4 MHz, CD$_2$Cl$_2$] (δ, ppm): −136.6 (d, 6 F, $^3$J$_{FF}$=21.8 Hz, o-F); −164.1 (t, 3 F, $^3$J$_{FF}$=20.6 Hz, p-F); −167.5 (m, 6 F, m-F).

NMR $^1$H [300.1 MHz, CD$_2$Cl$_2$] (δ, ppm): 1.56 (s, 1H, OH); 7.56-7.93 (m, 20H, Ph).

NMR $^{13}$C [75.5 MHz, CD$_2$Cl$_2$] (δ, ppm): 117.92 (d, $^1$J$_{PC}$=88.9 Hz, PC); 130.89 (d, $^3$J$_{PC}$=12.7 Hz, m-CH); 134.74 (d, $^2$J$_{PC}$=10.3 Hz, o-CH); 136.01 (bs, p-CH); 135.26, 136.99, 138.35, 140.16, 146.73, 149.86 (CF).

NMR $^{11}$B [96.3 MHz, CD$_2$Cl$_2$] (δ, ppm): −4.48 (s).

NMR $^{31}$P [121.5 MHz, CD$_2$Cl$_2$] (δ, ppm): 23.43 (s) (1J$_{PC}$=90.6 Hz, $^2$J$_{PC}$=11.3 Hz).

ESI-MS: ESI(+) [M=339, Ph$_4$P$^+$]; ESI(−) [M=529, B(C$_6$F$_5$)$_3$OH$^-$], [M=1397, [2×B(C$_6$F$_5$)$_3$OH$^-$+Ph$_4$P$^+$]$^-$].

IR [KBr]: ν(OH)=3693 cm$^{-1}$.

Examples of Type B Compounds

The type B compounds used hereafter are:
Cp$_2$ZrMe$_2$
Cp*ZrMe$_3$
Zr(CH$_2$Ph)$_4$.

These complexes are either commercial or synthesized by means of conventional methods described in the literature.

Example of Type I Compounds Preparation

Example 3

Preparation of [BMIM]$^+$[Cp$_2$Zr(Me)OB(C$_6$F$_5$)$_3$]$^-$

Compound A, [BMIM]$^+$[B(C$_6$F$_5$)$_3$OH]$^-$ (0.54 mmol), as prepared in Example 1, is brought into solution in toluene. The solution is added dropwise to a solution of compound B, Cp$_2$ZrMe$_2$ (0.54 mmol, 137 mg, 1 eq), in toluene at −25° C. The resulting yellow solution is kept under magnetic stirring for 2 h after returning to ambient temperature. Stirring is then stopped to allow decantation of the ionic complex [BMIM]$^+$ [Cp$_2$Zr(Me)OB(C$_6$F$_5$)$_3$]$^-$ in form of a lower red phase. The latter is isolated after canulating the yellow supernatent containing by-product Cp$_2$Zr(Me)OZr(Me)Cp$_2$.

The isolated type I compound [BMIM]$^+$[Cp$_2$Zr(Me)OB (C$_6$F$_5$)$_3$]$^-$ is characterized by fluorine, proton, carbon and boron NMR and by mass spectrometry. Boron NMR confirms the presence of the borate anion [—OB(C$_6$F$_5$)$_3$]$^-$: characteristic peak at −3.93 ppm. Proton NMR confirms the neutral character of Zr: Zr-Me characteristic peak at −0.19 ppm.

NMR $^{19}$F [282.4 MHz, CD$_2$Cl$_2$] (δ, ppm): −133.9 (d, 6 F, $^3J_{FF}$=22.5 Hz, o-F); −164.4 (t, 3 F, $^3J_{FF}$=20.8 Hz, p-F); −167.8 (m, 6 F, m-F).

NMR $^1$H [300.1 MHz, CD$_2$Cl$_2$] (δ, ppm): −0.19 (s, 3H, Zr—CH$_3$), 0.97 (t, 3H, $^3J_{HH}$=7.6 Hz, CH$_3$); 1.34 (sext, 2H, $^3J_{HH}$=7.6 Hz, CH$_2$); 1.81 (quint, 2H, $^3J_{HH}$=7.6 Hz, CH$_2$); 3.85 (s, CH$_3$); 4.1 (t, 2H, $^3J_{HH}$=7.6 Hz, CH$_2$); 5.77 (5, 10H, Cp); 7.15 (s, 2H, CH), 8.17 (s, 1H, CH).

NMR $^{13}$C [75.5 MHz, CD$_2$Cl$_2$] (δ, ppm): 13.39 (CH$_3$); 17.66 (Zr—CH$_3$); 19.68 (CH$_2$); 32.25 (CH$_2$); 36.66 (CH$_3$); 50.43 (CH$_2$); 109.69 (Cp); 122.41 (CH(BMIM+)); 123.76 (CH (BMIM+)); 135.06, 136.85 (CF), 138.34 (CH (BMIM+)); 138.35, 139.92, 146.58, 149.79 (CF).

NMR $^{11}$B [96.3 MHz, CD$_2$Cl$_2$] (δ, ppm): −3.93 (s).

ESI-MS: ESI(+) [M=139, BMIM$^-$]; ESI(−) [M=763, Cp$_2$Zr(Me)OB(C$_6$F$_5$)$_3$].

Example 4

Preparation of Q$^+$[Cp$_2$Zr(Me)OB(C$_6$F$_5$)$_3$] (Type I)

All the ionic complexes Q$^+$[Cp$_2$Zr(Me)OB(C$_6$F$_5$)$_3$]$^-$ associated with the various imidazolium, pyrrolidinium or phosphonium cations were prepared according to the same method as that described in Example 3 for cation Q$^+$: 1-butyl-3-methyl imidazolium with yields from 30% to 40%. These compounds are characterized by fluorine, proton, carbon and boron NMR and by mass spectrometry.

Q$^+$=imidazolium: Case of [BMMIM$^+$]; [EMIM$^+$]; [BBIM$^+$]:

Characterization of [BMMIM$^+$][Cp$_2$Zr(Me)OB(C$_6$F$_5$)$_3$$^-$] of Type I

NMR $^{19}$F [282.4 MHz, CD$_2$Cl$_2$] (δ, ppm): −133.9 (d, 6 F, $^3J_{FF}$=22.8 Hz, o-F); −164.6 (t, 3 F, $^3J_{FF}$=20.8 Hz, p-F); −167.9 (m, 6 F, m-F).

NMR $^1$H [300.1 MHz, CD$_2$Cl$_2$] (δ, ppm): −0.23 (s, 3H, Zr—CH$_3$), 0.97 (t, 3H, $^3J_{HH}$=7.6 Hz, CH$_3$); 1.35 (sext, 2H, $^3J_{HH}$=7.6 Hz, CH$_2$); 1.77 (quint, 2H, $^3J_{HH}$=7.6 Hz, CH$_2$); 2.53 (s, CH$_3$); 3.73 (s, 3H, CH$_3$); 3.99 (t, 2H, $^3J_{HH}$=7.6 Hz, CH$_2$); 5.74 (s, 10H, Cp); 7.12 (s, 2H, CH).

NMR $^{13}$C [75.5 MHz, CD$_2$Cl$_2$] (δ, ppm): 9.82 (CH$_3$); 13.41 (CH$_2$); 17.52 (Zr—CH$_3$); 19.89 (CH$_2$); 31.94 (CH$_2$); 35.76 (CH$_3$); 49.27 (CH$_2$); 109.66 (Cp); 121.52 (CH (BM-MIM+)); 122.98 (CH(BMMIM+)); 135.10, 136.74, 138.37; 139.95 (CF), 143.68 (C(CH$_3$) (BMMIM+)), 146.70, 149.89 (CF).

NMR $^{11}$B [96.3 MHz, CD$_2$Cl$_2$] (δ, ppm): −3.97 (s).

Characterization of [EMIM$^+$][C$_2$Zr(Me)OB(C$_6$F$_5$)$_3$$^-$]: Red Liquid of Type I NMR $^{19}$F [282.4 MHz, CD$_2$Cl$_2$] (δ, ppm): −134.0 (d, 6 F, $^3J_{FF}$=28.5 Hz, o-F); −164.5 (t, 3 F, $^3J_{FF}$=21.0 Hz, p-F); −167.9 (m, 6 F, m-F).

NMR $^1$H [300.1 MHz, CD$_2$Cl$_2$] (δ, ppm): −0.18 (s, 3H, Zr—CH$_3$), 1.50 (t, 6H, $^3J_{HH}$=7.6 Hz, CH$_3$); 3.84 (s, 3H, CH$_3$); 4.14 (quart, 4H, $^3J_{HH}$=7.6 Hz, CH$_2$); 5.77 (s, 10H, Cp); 7.16 (s, 1H, CH), 7.20 (s, 1H, CH), 8.67 (s, 1H, CH).

NMR $^{13}$C [75.5 MHz, CD$_2$Cl$_2$] (δ, ppm): 15.19 (CH$_3$); 17.82 (Zr—CH$_3$); 36.62 (CH$_2$); 49.94 (CH$_2$); 109.80 (Cp); 122.35 (CH(EMIM+)); 124.0 (CH(EMIM+)); 135.23, 136.99 (CF); 138.44 (CH(EMIM+)), 138.71, 140.30, 146.84, 150.02 (CF).

NMR $^{11}$B [96.3 MHz, CD$_2$Cl$_2$] (δ, ppm): −3.92 (s).

Characterization of [BBIM$^+$][Cp$_2$Zr(Me)OB(C$_6$F$_5$)$_3$$^-$]: Red Liquid of Type I NMR $^{19}$F [282.4 MHz, CD$_2$Cl$_2$] (δ, ppm): −134.0 (d, 6 F, $^3J_{FF}$=23.9 Hz, o-F); −164.4 (t, 3 F, $^3J_{FF}$=20.3 Hz, p-F); −167.8 (m, 6 F, m-F).

NMR $^1$H [300.1 MHz, CD$_2$Cl$_2$] (δ, ppm): −0.17 (s, 3H, Zr—CH$_3$), 0.97 (t, 6H, $^3J_{HH}$=7.3 Hz, CH$_3$); 1.35 (sext, 4H, $^3J_{HH}$=7.3 Hz, CH$_2$); 1.82 (quint, 4H, $^3J_{HH}$=7.3 Hz, CH$_2$); 4.1 (t, 4H, $^3J_{HH}$=7.3 Hz, CH$_2$); 5.78 (s, 10H, Cp); 7.19 (s, 2H, CH), 8.33 (s, 1H, CH).

NMR $^{13}$C [75.5 MHz, CD$_2$Cl$_2$] (δ, ppm): 13.31 (CH$_3$); 17.80 (Zr—CH$_3$); 19.76 (CH$_2$); 32.24 (CH$_2$); 50.53 (CH$_2$); 109.78 (Cp); 122.73 (CH(BBIM+)); 135.03 (CH(BBIM+), 135.03 (CF); 136.76, 138.36, 139.93, 146.74, 149.78 (CF).

NMR $^{11}$B [96.3 MHz, CD$_2$Cl$_2$] (δ, ppm): −3.88 (s).

Q$^+$=pyrrolidinium: Case of [BMpy$^+$]

Characterization of [BMpy$^+$][Cp$_2$Zr(Me)OB(C$_6$F$_5$)$_3$$^-$]: Red Liquid of Type I NMR $^{19}$F [282.4 MHz, CD$_2$Cl$_2$] (δ, ppm): −134.0 (d, 6 F, $^3J_{FF}$=25.2 Hz, o-F); −164.7 (t, 3 F, $^3J_{FF}$=20.2 Hz, p-F); −167.9 (m, 6 F, m-F).

NMR $^1$H [300.1 MHz, CD$_2$Cl$_2$] (δ, ppm): −0.22 (s, 3H, Zr—CH$_3$); 0.96 (t, 3H, $^3J_{HH}$=7.5 Hz, CH$_3$); 1.37 (sext, 2H, $^3J_{HH}$=7.5 Hz, CH$_2$); 1.68 (quint, 2H, $^3J_{HH}$=7.5 Hz, CH$_2$); 2.2 (bs, 4H, CH$_2$); 3.07 (s, 3H, CH$_3$); 3.31 (m, 2H, CH$_2$); 3.49-3.57 (m, 4H, CH$_2$); 5.74 (s, 10H, Cp).

NMR $^{13}$C [75.5 MHz, CD$_2$Cl$_2$] (δ, ppm): 13.64 (CH$_3$); 17.50 (Zr—CH$_3$); 20.07 (CH$_2$); 22.0 (CH$_2$); 26.11 (CH$_2$); 48.99 (CH$_3$); 64.59 (CH$_2$); 64.86 (CH$_2$); 109.68 (Cp); 134.99, 136.85, 138.38, 139.99, 146.67, 149.79 (CF).

NMR $^{11}$B [96.3 MHz, CD$_2$Cl$_2$] (δ, ppm): −3.95 (s).

Q$^+$=phosphonium: Case of [Bu$_4$P$^+$]; [Ph$_4$P$^+$]

Characterization of [Bu$_4$P$^+$][Cp$_2$Zr(Me)OB(C$_6$F$_5$)$_3$$^-$]: Yellow Powder of Type I NMR $^{19}$F [282.4 MHz, CD$_2$Cl$_2$] (δ, ppm): −133.9 (d, 6 F, $^3J_{FF}$=24.3 Hz, o-F); −164.6 (t, 3 F, $^3J_{FF}$=20.2 Hz, p-F); −167.9 (m, 6 F, m-F).

NMR $^1$H [300.1 MHz, CD$_2$Cl$_2$] (δ, ppm): −0.21 (s, 3H, Zr—CH$_3$); 0.98 (t, 12H, $^3J_{HH}$=6.9 Hz, CH$_3$); 1.46-1.51 (m, 16H, CH$_2$); 1.93-2.03 (m, 8H, PCH$_2$); 5.75 (s, 10H, Cp).

NMR $^{13}$C [75.5 MHz, CD$_2$Cl$_2$] (δ, ppm): 13.32 (CH$_3$); 17.58 (Zr—CH$_3$); 18.99 (d, $^1J_{PC}$=48.3 Hz, PCH$_2$); 23.70 (d, $^2J_{PC}$=4.7 Hz, CH$_2$); 24.21 (d, $^3J_{PC}$=15.5 Hz, CH$_2$); 109.65 (Cp); 135.12, 136.78, 138.33, 139.99, 146.65, 149.81 (CF).

$^{31}$P NMR [121.5 MHz, CD$_2$Cl$_2$] (δ, ppm): 33.40 (s) (1$J_{PC}$=47.6 Hz, $^2J_{PC}$=14.9 Hz).

NMR $^{11}$B [96.3 MHz, CD$_2$Cl$_2$] (δ, ppm): −3.95 (s).

Characterization [Ph$_4$P$^+$][Cp$_2$Zr(Me)OB(C$_6$F$_5$)$_3$$^-$]: Yellow Liquid of Type I NMR $^{19}$F [282.4 MHz, CD$_2$Cl$_2$] (δ, ppm): −134.0 (d, 6 F, $^3J_{FF}$=21.7 Hz, o-F); −164.7 (t, 3 F, $^3J_{FF}$=20.2 Hz, p-F); −167.9 (m, 6 F, m-F).

NMR $^1$H [300.1 MHz, CD$_2$Cl$_2$] (δ, ppm): −0.23 (s, 3H, Zr—CH$_3$); 5.72 (s, 10H, Cp); 7.56-7.76 (m, 20H, Ph).

NMR $^{13}$C [75.5 MHz, CD$_2$Cl$_2$] (δ, ppm): 17.47 (Zr—CH$_3$); 109.63 (Cp); 117.92 (d, $^1J_{PC}$=90.3 Hz, PC); 130.98 (d, $^3J_{PC}$=13.1 Hz, m-CH); 134.76 (d, $^2J_{PC}$=10.0 Hz, o-CH); 136.01 (d, $^4J_{PC}$=2.8 Hz, p-CH); 135.24, 136.73, 138.54, 139.89, 146.65, 149.91 (CF).

NMR $^{31}$P [121.5 MHz, CD$_2$Cl$_2$] (δ, ppm): 23.43 (s) ($^1J_{PC}$=90.2 Hz, $^2J_{PC}$=11.4 Hz).

NMR $^{11}$B [96.3 MHz, CD$_2$Cl$_2$] (δ, ppm): −3.98 (s).

Example 5

Preparation of [BMIM]$^+$[Cp*ZrMe$_2$OB(C$_6$F$_5$)$_3$]$^-$ (Type I)

Compound A, [BMIM]$^+$[B(C$_8$F$_8$)$_3$OH]$^-$ (0.38 mmol) as prepared in Example 1, is brought into solution in toluene. The solution obtained is added dropwise to a solution of the type B compound, Cp*ZrMe$_3$ (0.38 mmol, 102 mg, 1 eq), in toluene at −25° C. After returning to ambient temperature, the yellow solution is further stirred for 2 h and it turns yellow-orangey.

NMR spectroscopy analysis of the solution obtained shows the presence of the expected compound [BMIM]$^+$ [Cp*ZrMe$_2$OB(C$_8$F$_8$)$_3$]$^-$. The anionic character of the boron is confirmed by boron NMR: characteristic peak at −4.17 ppm for the borate anion [—OB(C$_6$F$_5$)$_3$]$^-$. Proton NMR confirms the neutral character of Zr: Zr-Me characteristic peak at −0.14 ppm.

Characterization of [BMIM]$^+$[Cp*ZrMe$_2$OB(C$_6$F$_5$)$_3$]$^-$

NMR $^{19}$F [282.4 MHz, C$_7$D$_8$] (δ, ppm): −133.9 (d, 6 F, $^3J_{FF}$=23.3 Hz, o-F); −163.6 (t, 3 F, $^3J_{FF}$=20.8 Hz, p-F); −167.0 (m, 6 F, m-F).

NMR $^1$H [300.1 MHz, C$_7$D$_8$] (δ, ppm): −0.14 (s, 3H, Zr—CH$_3$), 0.69 (t, 3H, $^3J_{HH}$=7.6 Hz, CH$_3$); 0.81 (sextet, 2H, $^3J_{HH}$=7.6 Hz, CH$_2$); 1.01 (quintet, 2H, $^3J_{HH}$=7.6 Hz, CH$_2$); 1.96 (s, 15H, Cp*(Me)); 2.63 (s, CH$_3$); 2.99 (t, 2H, $^3J_{HH}$=7.6 Hz, CH$_2$); 5.79 (d, 1H, $^3J_{HH}$=2.0 Hz, CH); 5.83 (d, 1H, $^3J_{HH}$=2.0 Hz, CH); 6.28 (s, 1H, CH).

NMR $^{13}$C [75.5 MHz, C$_7$D$_8$] (δ, ppm): 10.83 (COMe)); 13.09 (CH$_3$); 19.38 (CH$_2$); 31.55 (CH$_2$); 35.15 (CH$_3$); 32.32 (Zr—CH$_3$); 49.60 (CH$_2$); 117.99 (Cp*); 121.54 (CH (BMIM+)); 123.0 (CH(BMIM+)); 135.27, 136.72 (CF); 137.07 (CH(BMIM+)); 138.50, 140.09, 146.85, 149.99 (CF).

NMR $^{11}$B [96.3 MHz, C$_7$H$_8$—C$_6$D$_6$] (δ, ppm): −4.17 (s).

Examples of Type II Complexes

Example 6

Preparation of [EMIM]$_2$$^{2+}$[Zr(CH$_2$Ph)$_2$(OB(C$_6$F$_5$)$_3$)$_2$]$^{2-}$ (Type II)

Compound A, [EMIM]$^+$[B(C$_8$F$_5$)$_3$OH]$^-$ (0.48 mmol, 2 eq), as described in Example 2, is brought into solution in toluene. The solution is added dropwise to a solution of compound B, Zr(CH$_2$Ph)$_4$ (0.24 mmol, 109 mg, 1 eq) in toluene, at −25° C. After returning to ambient temperature, the yellow solution is further stirred for 2 h, then stirring is stopped to allow decantation of the ionic complex [EMIM]$_2$$^{2+}$[Zr (CH$_2$Ph)$_2$(OB(C$_6$F$_5$)$_3$)$_2$]$^{2-}$ of type B, in form of a lower yellow phase. Yield: 32%. Compound [EMIM]$_2$$^{2+}$ [Zr(CH$_2$Ph)$_2$ (OB(C$_6$F$_5$)$_3$)$_2$]$^{2-}$ is characterized by proton, carbon, boron and fluorine NMR. Boron NMR confirms the presence of the borate anion [—OB(C$_6$F$_5$)$_3$]$^-$ at −4.94 ppm.

NMR $^{19}$F [282.4 MHz, CD$_2$Cl$_2$] (δ, ppm): −134.8 (d, 6 F, $^3J_{FF}$=27.5 Hz, o-F); −166.5 (t, 3 F, $^3J_{FF}$=21.4 Hz, p-F); −169.1 (m, 6 F, m-F).

NMR $^1$H [300.1 MHz, CD$_2$Cl$_2$] (δ, ppm): 1.40 (t, 6H, $^3J_{HH}$=7.4 Hz, CH$_3$); 1.66, 1.83 (s, 2H, Zr—CH$_2$), 3.64 (s, 3H, CH$_3$); 3.96 (quartet, 4H, $^3J_{HH}$=7.4 Hz, CH$_2$); 6.39-7.30 (m, Ph); 6.99 (m, 1H, CH), 7.03 (m, 1H, CH), 7.66 (s, 1H, CH).

NMR $^{13}$C [75.5 MHz, CD$_2$Cl$_2$] (δ, ppm): 15.01 (CH$_3$); 36.43 (CH$_3$); 45.90 (CH$_2$); 48.91, 55.83 (Zr—CH$_2$); 122.21 (CH(EMIM+)); 124.06 (CH(EMIM+)); 134.61 (CH (EMIM+)); 125.67-129.70 (Ph); 134.60-149.89 (CF).

NMR $^{11}$B [96.3 MHz, CD$_2$Cl$_2$] (δ, ppm): −4.94 (s).

Examples of Reaction of the Type I Compound with a Lewis Acid

Example 7

Preparation of [BBIM]$^+$[Cp$_2$Zr$^+$OB$^-$(C$_6$F$_5$)$_3$][MeB (C$_6$F$_5$)$_3$]$^-$ The reaction of the ionic complex of type I [BBIM]$^+$[Cp$_2$Zr (Me)OB(C$_6$F$_5$)$_3$]$^-$ (43 mg, 0.045 mmol) as prepared in Example 4, solubilized in dichloromethane with a stoichiometric proportion of B(C$_6$F$_5$)$_3$ (23 mg, 0.045 mmol), was studied by $^{11}$B, $^{19}$F, $^{13}$C, $^1$H NMR. The formation of anion [MeB(C$_6$F$_5$)$_3$]$^-$ is observed, as well as the formation of several zirconocene products identified by their Cp resonances ($^1$H NMR: 5.96, 6.14, 6.16, 6.34; $^{13}$C NMR: 113.75, 114.01, 114.19, 115.55) and a large $^{11}$B NMR resonance (−2.96 ppm) characteristic of structures containing a —OB(C$_6$F$_5$)$_3$ fragment. These analyses confirm the formation of a cationic zirconium complex of [BBIM]$^+$[Cp$_2$Zr$^+$OB$^-$(C$_6$F$_5$)$_3$][MeB (C$_6$F$_5$)$_3$]$^-$ type.

Characterization of anion [MeB(C$_6$F$_5$)$_3$]$^-$: $^{19}$F NMR [282.4 MHz, CD$_2$Cl$_2$] (δ, ppm): −134.2 (m, o-F); −165.7 (m, p-F); −168.1 (m, m-F). $^1$H NMR [300.1 MHz, CD$_2$Cl$_2$] (δ, ppm): 0.48. $^{13}$C NMR [75.5 MHz, CD$_2$Cl$_2$] (δ, ppm): 10.12. $^{11}$B NMR [96.3 MHz, CD$_2$Cl$_2$] (δ, ppm): −15.35.

Example 8

Preparation of [Bu$_4$P]$^+$[Cp$_2$Zr$^+$OB$^-$(C$_6$F$_5$)$_3$][MeB (C$_6$F$_5$)$_3$]$^-$ in the Ionic Liquid [BMpy]$^+$[NTf$_2$]$^-$ Solubilization of Complex [Bu$_4$P]$^+$[Cp$_2$Zr(Me)OB (C$_6$F$_5$)$_3$]$^-$ in an Ionic Liquid:

In an NMR tube, the ionic complex [Bu$_4$P]$^+$[Cp$_2$Zr(Me) OB(C$_6$F$_5$)$_3$]$^-$ (108 mg, 0.11 mmol) of type I as prepared in Example 4 is solubilized in CD$_2$Cl$_2$ (0.7 mL) and a proportion of ionic liquid [BMpy]$^+$[NTf$_2$]$^-$ (0.1 mL) is introduced. The solubilization of complex [Bu$_4$P]$^+$[Cp$_2$Zr(Me)OB(C$_6$F$_5$)$_3$]$^-$ in the medium is observed visually (homogenous yellow solution) and by $^{11}$B NMR.

$^{11}$B NMR [96.3 MHz, CD$_2$Cl$_2$] (δ, ppm):
[Bu$_4$P]$^+$[CP$_2$Zr(Me)OB(C$_6$F$_5$)$_3$]$^+$ (alone, before addition of the ionic liquid [BMpy]$^+$[NTf$_2$]$^-$): −3.95.

[Bu$_4$P]$^+$[Cp$_2$Zr(Me)OB(C$_6$F$_5$)$_3$]$^+$ with 0.1 mL of ionic liquid [BMpy]$^+$[NTf$_2$]$^-$: −3.94.

Reaction of Complex [Bu$_4$P]$^+$[Cp$_2$Zr(Me)OB(C$_6$F$_5$)$_3$]$^-$ with B(C$_6$F$_5$)$_3$ in the Ionic Liquid:

A stoichiometric proportion of B(C$_6$F$_5$)$_3$ (54 mg, 0.11 mmol) is added to the type I complex solution [Bu$_4$P]$^+$[Cp$_2$Zr (Me)OB(C$_6$F$_5$)$_3$]$^+$ (108 mg, 0.11 mmol) in the mixture CD$_2$Cl$_2$ (0.7 mL)/[BMpy]$^+$[NTf$_2$]$^-$ (0.1 mL). The reaction is followed by $^{11}$B NMR with immediate formation of anion [MeB(C$_6$F$_5$)$_3$]$^-$ (resonance at −15.39 ppm). Another $^{11}$B NMR resonance at −3.09 ppm (characteristic of a —OB (C$_6$F$_5$)$_3^-$ fragment) can be attributed to a zirconocene major product with a Cp resonance that can be observed by $^1$H NMR at 6.19 ppm and $^{13}$C NMR at 114.02 ppm. This compound is also detected by $^{19}$F NMR by the following resonances: −134.3 (dd, 6 F, $^3J_{FF}$=9.7 Hz, $^3J_{FF}$=9.9 Hz, o-F), −162.9 (t, 3 F, $^3J_{FF}$=20.4 Hz, p-F), −167.2 (m, 6 F, m-F). All of these characterizations correspond to the formation of complex [Bu$_4$P][Cp$_2$Zr$^+$OB$^-$(C$_6$F$_5$)$_3$][MeB(C$_6$F$_5$)$_3$]$^-$.

Example of Ethylene Conversion Catalysis

Example 9

Polymerization of Ethylene with Type I Complex [BMIM]$^+$[Cp*ZrMe$_2$OB(C$_6$F$_5$)$_3$]$^-$ to Which Lewis Acid B(C$_6$F$_5$)$_3$ is Added In a 250-ml autoclave, provided with a double wall and a bar magnet, dried beforehand under vacuum at 90° C. for 4 hours, and passivated with a solution of MAO in toluene, 50 ml toluene are added at 20° C. and in an ethylene atmosphere. The type I complex described in Example 5, [BMIM]$^+$ [Cp*ZrMe$_2$OB(C$_6$F$_5$)$_3$]$^-$, (231.4 mg) in 9 mL toluene is added, then 0.9 equivalent of B(C$_6$F$_5$)$_3$ in 2 ml toluene is added under stirring. The ethylene pressure is set at 2 MPa and it is kept constant in the reactor, and the temperature is maintained at 20° C. Stirring is continued for 300 minutes. An ethylene consumption of 22 g is observed. Stirring is stopped, the reactor is depressurized and the volume of gas that has left is measured in a gas meter. This gas is analyzed by gas chromatography (GC). At 10° C., a liquid phase (37 g) and a solid (17 g) neutralized through ethanol injection (1.5 ml) are withdrawn from the reactor. The only reaction product is polyethylene.

Example 10

Polymerization of Ethylene with Type I Complex [BMIM]$^+$[Cp$_2$ZrMeOB(C$_6$F$_5$)$_3$]$^-$ to Which MAO is Added The same reactor as in Example 9 is used, under the same operating conditions, except that type I complex BMIM]$^+$ [Cp$_2$ZrMeOB(C$_6$F$_5$)$_3$]$^-$ (130 mg) in 3 ml toluene, to which 150 eq methylaluminoxane (MAO 10% in toluene) is added, is introduced into the reactor. The pressure is set at 2 MPa ethylene and the temperature is 20° C. Stirring is maintained for 15 minutes. An ethylene consumption of 10 g is observed. The same treatment as in Example 9 is then performed. Analysis shows the formation of polyethylene (7.5 g).

The invention claimed is:

1. A group 4 organometallic compound supported on anions by means of a covalent metal-oxygen bond, of formula I or II:

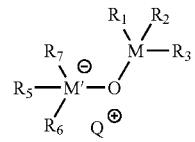

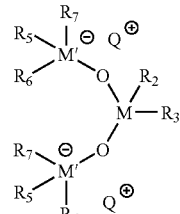

wherein:
M represents titanium, zirconium or hafnium,
M' represents boron or aluminium,
R$_1$, R$_2$, R$_3$, identical or different, represent halogenides or organic radicals having 1 to 30 carbon atoms,
R$_5$, R$_6$, R$_7$, identical or different, represent organic radicals having 1 to 30 carbon atoms, and
Q$^+$ represents an organic or inorganic cation.

2. A compound as claimed in claim 1, wherein groups R$_5$, R$_6$, R$_7$, identical or different, represent alkyl radicals having 1 to 30 carbon atoms, saturated or non-saturated, cycloalkyl or aromatic groups, aryl or aralkyl groups, optionally substituted, hydrocarbyl radicals wherein one or more hydrogen atoms are replaced by halogenides or groups comprising at least one heteroelement that is oxygen, nitrogen, sulfur or silicon of the alkoxy, aryloxy or amidide groups.

3. A compound as claimed in claim 1, wherein R$_1$, R$_2$, R$_3$ represent alkyl, cycloalkyl or aryl groups, optionally substituted, cyclopentadienyls, optionally substituted, alkoxy, aryloxy, amidide, hydrido, carboxylate, oxalate, β-diketiminate, iminopyrrolide, amidinate or boratabenzene groups.

4. A compound as claimed in claim 1, of formula I, wherein at least two of the three groups R$_1$, R$_2$, R$_3$ are hydrocarbyl radicals that are alkyl, cycloalkyl, aryl or aralkyl groups.

5. A compound as claimed in claim 1, of formula II, wherein R$_2$ and R$_3$ are hydrocarbyl radicals that are alkyl, cycloalkyl, aryl or aralkyl groups.

6. A compound as claimed in claim 1, wherein cation Q$^+$ is:

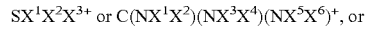

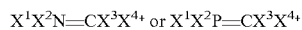

wherein X$^1$, X$^2$, X$^3$, X$^4$, X$^5$ and X$^6$, identical or different, represent hydrogen, or hydrocarbyl radicals having 1 to 30 carbon atoms.

7. A compound as claimed in claim 1, wherein Q$^+$ is derived from nitrogen-containing and/or phosphorus-containing heterocycles comprising 1, 2 or 3 atoms of nitrogen and/or phosphorus, of the formulas:

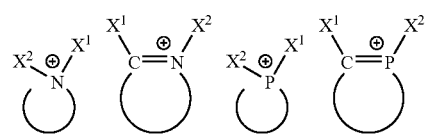

wherein the heterocycles consist of 4 to 10 atoms, and $X^1$ and $X^2$, identical or different, represent hydrogen, or hydrocarbyl radicals having 1 to 30 carbon atoms.

8. A method for synthesis of a compound as claimed in claim 1, wherein a borate or aluminate compound A comprising at least one hydroxy group is reacted with a compound B of a group 4 transition metal, optionally in the presence of a solvent, wherein compound A has the formula:

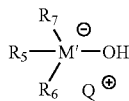
A wherein M' represents boron or aluminium, $Q^+$ represents an organic or inorganic cation, $R_5$, $R_6$ and $R_7$, identical or different, represent organic radicals having 1 to 30 carbon atoms, and compound B has the formula:

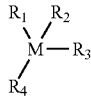
B wherein M represents titanium, zirconium or hafnium, $R_1$, $R_2$, $R_3$ and $R_4$, identical or different, represent halogenides or organic radicals having 1 to 30 carbon atoms.

9. A method as claimed in claim 8, wherein the solvent is an organic solvent, an ionic liquid, and/or mixtures thereof.

10. A method as claimed in claim 8, wherein the molar ratio of A to B ranges between 0.1/1 and 100/1.

11. A method as claimed in claim 8, wherein the reaction temperature ranges between −100° C. and 150° C.

12. A mixture of group 4 organometallic compounds supported on borate or aluminate anions by means of at least one covalent metal-oxygen bond, obtained by reaction between at least one compound A comprising at least one hydroxy group and at least one compound B, optionally in the presence of a solvent, compound A being of the formula:

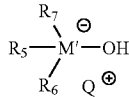
A wherein M' represents boron or aluminium, $Q^+$ represents an organic or inorganic cation, $R_5$, $R_6$ and $R_7$, identical or different, represent organic radicals having 1 to 30 carbon atoms, compound B of the formula:

B wherein M represents titanium, zirconium or hafnium, $R_1$, $R_2$, $R_3$ and $R_4$, identical or different, represent halogenides or organic radicals having 1 to 30 carbon atoms.

13. A mixture as claimed in claim 12, characterized in that compound A is selected from among butyl-3-methyl-1-imidazolium tris-pentafluorophenyl-hydroxyborate, 1 butyl-2,3-dimethylmidazolium tris-pentafluorophenyl-hydroxyborate, 1-ethyl-3-methylimidazolium tris-pentafluorophenyl-hydroxyborate, 1-butyl-3-butylimidazolium tris-pentafluorophenyl-hydroxyborate, N,N-butylmethylpyrrolidinium, tris-pentafluorophenyl-hydroxyborate, tetrabutylphosphonium tris-pentafluorophenyl-hydroxyborate, tetraphenylphosphonium tris-pentafluorophenyl-hydroxyborate, butyl-3-methyl-1-imidazolium tris-pentafluorophenyl-hydroxyaluminate, butyl-3-methyl-1-imidazolium tris-phenyl-hydroxyborate, butyl-3-methyl-1-imidazolium tris-[3,5-bis(tri-fluoromethyl)phenyl]-hydroxyborate.

14. A mixture as claimed in claim 12, wherein at least two hydrocarbyl radicals $R_1$, $R_2$, $R_3$ and $R_4$, identical or different, are alkyl, cycloalkyl, aryl or aralkyl groups.

15. A mixture as claimed in claim 12, wherein compound B is $ZrCl_4$, $Zr(CH_2Ph)_4$, $Zr(CH_2CMe_3)_4$, $Zr(CH_2SiMe_3)_4$, $Zr(CH_2Ph)_3Cl$, $Zr(CH_2CMe_3)_3Cl$, $Zr(CH_2SiMe_3)_3Cl$, $Zr(CH_2Ph)_2Cl_2$, $Zr(CH_2CMe_3)_2Cl_2$, $Zr(CH_2SiMe_3)_2Cl_2$, $Zr(NMe_2)_4$, $Zr(NEt_2)_4$, $Zr(NMe_2)_2Cl_2$, $Zr(NEt_2)_2Cl_2$, $Zr(N(SiMe_3)_2)_2Cl_2$, $Cp_2ZrMe_2$, $CpZrMe_3$, $Cp^*ZrMe_3$ ($Cp^*$=penta-methylcyclopentadienyl), $HfCl_4$, $Cp_2HfMe_2$, $CpHfMe_3$, $Hf(CH_2Ph)_4$, $Hf(CH_2CMe_3)_4$, $Hf(CH_2SiMe_3)_4$, $Hf(CH_2Ph)_3Cl$, $Hf(CH_2CMe_3)_3Cl$, $Hf(CH_2SiMe_3)_3Cl$, $Hf(CH_2Ph)_2Cl_2$, $Hf(CH_2CMe_3)_2Cl_2$, $Hf(CH_2SiMe_3)_2Cl_2$, $Hf(NMe_2)_4$, $Hf(NEt_2)_4$ or $Hf(N(SiMe_3)_2)_2Cl_2$.

16. A catalytic composition comprising:
i) at least one compound of formula I or II

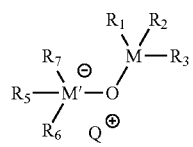
I

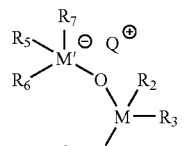
II wherein:
M represents titanium, zirconium or hafnium,
M' represents boron or aluminium,
$R_1$, $R_2$, $R_3$, identical or different, represent halogenides or organic radicals having 1 to 30 carbon atoms,
$R_5$, $R_6$, $R_7$, identical or different, represent organic radicals having 1 to 30 carbon atoms, and
$Q^+$ represents an organic or inorganic cation,
ii) at least one activator agent, and
iii) optionally a solvent.

17. A catalytic composition as claimed in claim 16, wherein the activator agent is a Lewis acid, a Bronsted acid, an alkylating agent or any a compound that hydrogenolyzes a metal-carbon bond (M-C).

18. A catalytic composition as claimed in claim 16, wherein the activator agent is aluminoxanes, organoaluminiums, aluminium halogenides, aluminates, boranes, borates, organozincs, hydrogen or mixtures thereof.

19. A catalytic composition as claimed in claim 16, wherein the solvent is organic solvents, ionic liquids or mixtures thereof.

20. A catalytic composition as claimed in claim 16, wherein the molar ratio of I or II to activator agent ranges between 1/10,000 and 100/1.

21. A catalytic composition as claimed in claim 20, wherein the molar ratio of I or II to activator agent preferably ranges between 1/2000 and 1/1 when the activator agent is an alkylating agent.

22. A catalytic composition as claimed in claim 20, wherein the molar ratio of I or II to activator agent preferably ranges between 1/50 and 1/1 when the activator agent is a Lewis acid, a Bronsted acid or any compound that hydrogenolyzes a metal-carbon bond of I or II, for the organometallic compounds of formula I, of which at least two of the three groups $R_1$, $R_2$ and $R_3$ are hydrocarbyl radicals, and for the organometallic compounds of general formula II, of which the two groups $R_2$ and $R_3$ are hydrocarbyl groups.

23. A method for oligomerization or polymerization of olefins comprising subjecting said olefins to oligomerization or polymerization conditions in a catalytic reaction in the presence of a catalytic composition as claimed in claim 16.

24. A catalytic composition resulting from contacting:
   i) at least one borate or aluminate compound A comprising at least one hydroxy group, of the formula:

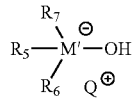

A wherein M' represents boron or aluminium, $Q^+$ represents an organic or inorganic cation, $R_5$, $R_6$ and $R_7$, identical or different, represent organic radicals having 1 to 30 carbon atoms, ii) at least one compound B of a group 4 transition metal of the formula:

B wherein M represents titanium, zirconium or hafnium, $R_1$, $R_2$, $R_3$ and $R_4$, identical or different, represent halogenides or organic radicals having 1 to 30 carbon atoms,
   iii) at least one activator agent,
   iv) optionally a solvent.

25. A catalytic composition as claimed in claim 16, wherein the molar ratio of B to activator agent ranges between 1/10,000 and 100/1.

26. A catalytic composition as claimed in claim 25, wherein the molar ratio of B to activator agent preferably ranges between 1/50 and 1/1 when the activator agent is a Lewis acid, a Bronsted acid or any compound that hydrogenolyzes a metal-carbon bond of B, for the organometallic compounds of formula B, of which at least three of the four groups $R_1$, $R_2$, $R_3$ and $R_4$ are hydrocarbyl radicals.

27. A catalytic composition as claimed in claim 25, wherein the molar ratio of B to activator agent preferably ranges between 1/2000 and 1/1 when the activator agent is an alkylating agent.

28. A catalytic composition as claimed in claim 16, wherein the molar ratio of A to B ranges between 0.1/1 and 100/1.

* * * * *

UNITED STATES PATENT AND TRADEMARK OFFICE
CERTIFICATE OF CORRECTION

PATENT NO.       : 8,470,940 B2
APPLICATION NO.  : 12/667557
DATED            : June 25, 2013
INVENTOR(S)      : Bibal et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 695 days.

Signed and Sealed this
Eighth Day of September, 2015

Michelle K. Lee
*Director of the United States Patent and Trademark Office*